United States Patent
Isaacson et al.

(10) Patent No.: US 11,956,599 B2
(45) Date of Patent: *Apr. 9, 2024

(54) SUB-SURFACE INDICATOR LIGHTING

(71) Applicant: Cochlear Limited, Macquarie University (AU)

(72) Inventors: Nathan Isaacson, North Sydney (AU); Jan Patrick Frieding, Grose Vale (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/842,394

(22) Filed: Jun. 16, 2022

(65) Prior Publication Data
US 2022/0394400 A1 Dec. 8, 2022

Related U.S. Application Data

(63) Continuation of application No. 16/973,247, filed as application No. PCT/IB2019/056073 on Jul. 16, 2019, now Pat. No. 11,388,530.
(Continued)

(51) Int. Cl.
*H04R 25/00* (2006.01)
*F21V 19/00* (2006.01)
(Continued)

(52) U.S. Cl.
CPC ....... *H04R 25/604* (2013.01); *F21V 19/0015* (2013.01); *H04R 7/16* (2013.01);
(Continued)

(58) Field of Classification Search
CPC .... H04R 25/604; H04R 25/609; H04R 19/04; H04R 2201/003; H04R 2225/021; H04R 2225/67
See application file for complete search history.

(56) References Cited

U.S. PATENT DOCUMENTS

| 7,248,926 B2 | 7/2007 | Woods |
| 9,392,384 B2 | 7/2016 | Crawford et al. |

(Continued)

FOREIGN PATENT DOCUMENTS

| CN | 101427593 A | 5/2009 |
| CN | 103475983 A | 12/2013 |

(Continued)

OTHER PUBLICATIONS

International Search Report and Written Opinion received in international application No. PCT/IB2019/056073, dated Dec. 13, 2019 (11 pages).

*Primary Examiner* — Sunita Joshi
(74) *Attorney, Agent, or Firm* — Edell, Shapiro & Finnan, LLC

(57) ABSTRACT

Presented herein are devices/apparatuses having indicator lights (visual indicators), such as light emitting diodes (LEDs), positioned underneath/below the outer surface of a housing of the device. However, the indicator lights positioned below the outer surface of the housing, sometimes referred to herein as "sub-surface" or "sub-housing" indicator lights, are optically coupled to the outer surface of the housing via one or more optical connectors (e.g., light guides, light pipes, light diffusers, etc.). As such, the light emitted by the sub-surface indicator lights is still visible at the outer surface of the device housing.

20 Claims, 9 Drawing Sheets

Related U.S. Application Data

(60) Provisional application No. 62/700,407, filed on Jul. 19, 2018.

(51) Int. Cl.
    *H04R 7/16*     (2006.01)
    *H04R 19/04*     (2006.01)
    *A61N 1/36*     (2006.01)
    *F21Y 113/10*     (2016.01)
    *F21Y 115/10*     (2016.01)

(52) U.S. Cl.
    CPC ........... *H04R 19/04* (2013.01); *H04R 25/609* (2019.05); *A61N 1/36038* (2017.08); *F21Y 2113/10* (2016.08); *F21Y 2115/10* (2016.08); *H04R 2201/003* (2013.01); *H04R 2225/021* (2013.01); *H04R 2225/67* (2013.01)

(56) References Cited

U.S. PATENT DOCUMENTS

| | | | |
|---|---|---|---|
| 9,894,428 | B1 | 2/2018 | Chamberlin et al. |
| 9,906,881 | B2 | 2/2018 | Darley et al. |
| 2005/0094832 | A1* | 5/2005 | Song ................ H04R 19/00 381/174 |
| 2006/0245611 | A1 | 11/2006 | Jørgensen |
| 2011/0046730 | A1 | 2/2011 | Meskens |
| 2015/0012058 | A1 | 1/2015 | Crawford et al. |
| 2015/0163606 | A1 | 6/2015 | Halverson |
| 2015/0323456 | A1 | 11/2015 | Agashe et al. |
| 2016/0345086 | A1* | 11/2016 | Chamberlin ........... H04R 1/342 |
| 2017/0311099 | A1 | 10/2017 | Vardfjäll et al. |
| 2017/0318396 | A1* | 11/2017 | Brioschi ................ H04R 3/005 |
| 2021/0243539 | A1 | 8/2021 | Isaacson et al. |

FOREIGN PATENT DOCUMENTS

| | | |
|---|---|---|
| EP | 3136752 A1 | 3/2017 |
| WO | 2016187868 A1 | 12/2016 |

\* cited by examiner

SUB-SURFACE INDICATOR LIGHTING

BACKGROUND

Field of the Invention

The present invention relates generally to indicator lights positioned beneath the surface of a device housing.

Related Art

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In one aspect, an apparatus is provided. The apparatus comprises: a housing including at least one acoustic port; a microphone positioned within the housing in alignment with the acoustic port; at least one optical connector positioned within the acoustic port; and at least one indicator light positioned within the housing, wherein the at least one indicator light is optically coupled to the acoustic port via the optical connector such that light emitted from the at least one indicator light is visible outside of the housing via the acoustic port.

In another aspect, an apparatus is provided. The apparatus comprises: a housing comprising at least one acoustic port, an outer surface, and an inner surface; a printed circuit board (PCB) positioned within the housing adjacent to the acoustic port; a microelectromechanical systems (MEMS) microphone mounted on the PCB in-line with the acoustic port; at least one indicator light co-located with the MEMS microphone on the PCB below the inner surface of the housing; and at least one optical connector optically coupling the at least one indicator light to the outer surface of the housing.

BRIEF DESCRIPTION OF THE DRAWINGS

Embodiments of the present invention are described herein in conjunction with the accompanying drawings, in which.

DETAILED DESCRIPTION

Presented herein are devices/apparatuses having indicator lights (indicator lights), such as light emitting diodes (LEDs), positioned underneath/below the outer surface of a housing of the device. However, the indicator lights positioned below the outer surface of the housing, sometimes referred to herein as "sub-surface" or "sub-housing" indicator lights, are optically coupled to the outer surface of the housing via one or more optical connectors (e.g., light guides, light pipes, light diffusers, etc.). As such, the light emitted by the sub-surface indicator lights is still visible at the outer surface of the device housing.

Merely for ease of description, embodiments are primarily described herein with reference to one illustrative device/apparatus, namely the external component of a cochlear implant. However, it is to be appreciated that the techniques presented herein may also be used with a variety of other devices that include indicator lights. For example, the techniques presented herein may be used with other auditory prostheses, including acoustic hearing aids, bone conduction devices, middle ear auditory prostheses, direct acoustic stimulators, auditory brain stimulators), etc., and/or other devices, such as mobile computing devices (e.g., mobile phones, tablet computers, etc.).

Figure 1A:
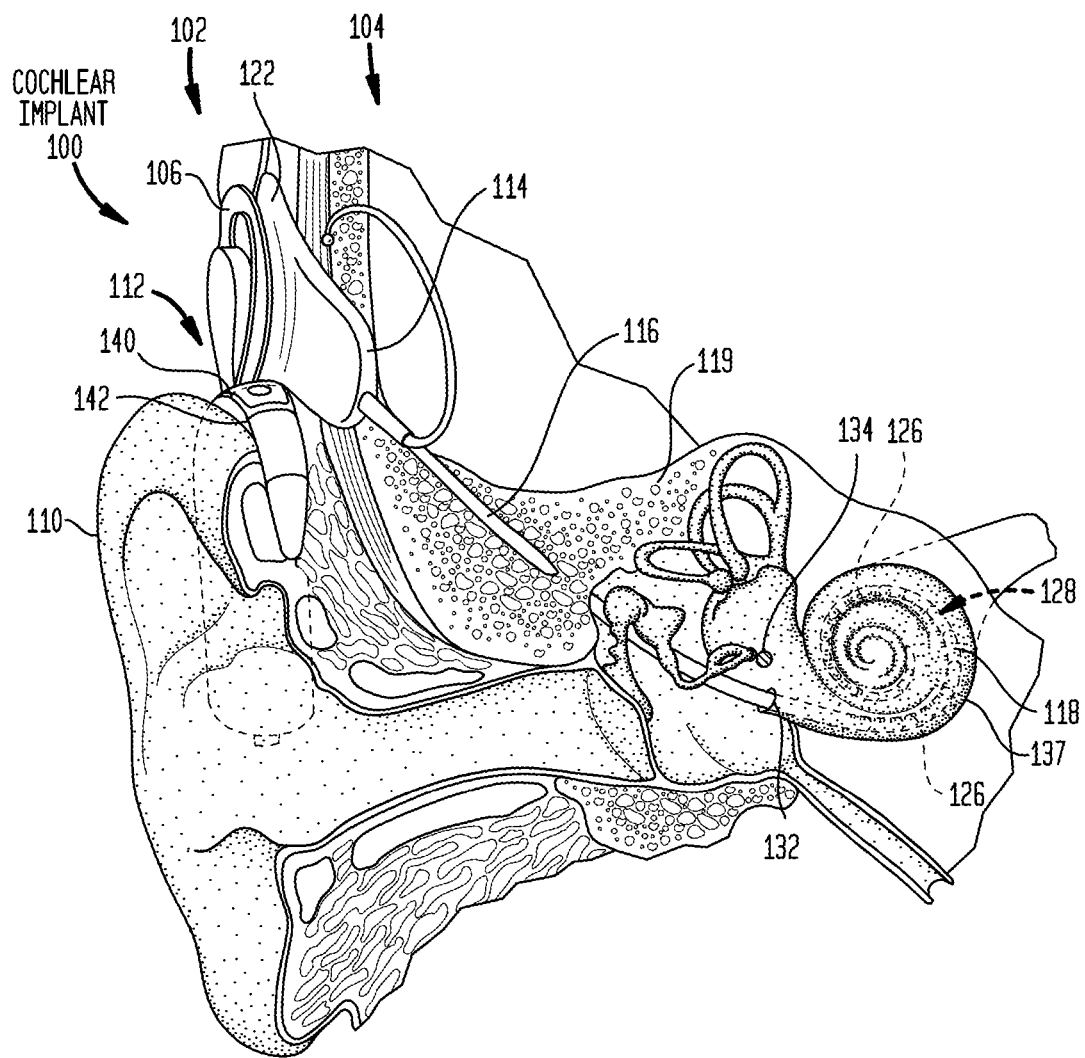
FIG. 1A is a schematic diagram illustrating a cochlear implant, in accordance with certain embodiments presented herein.
Figure 1B:
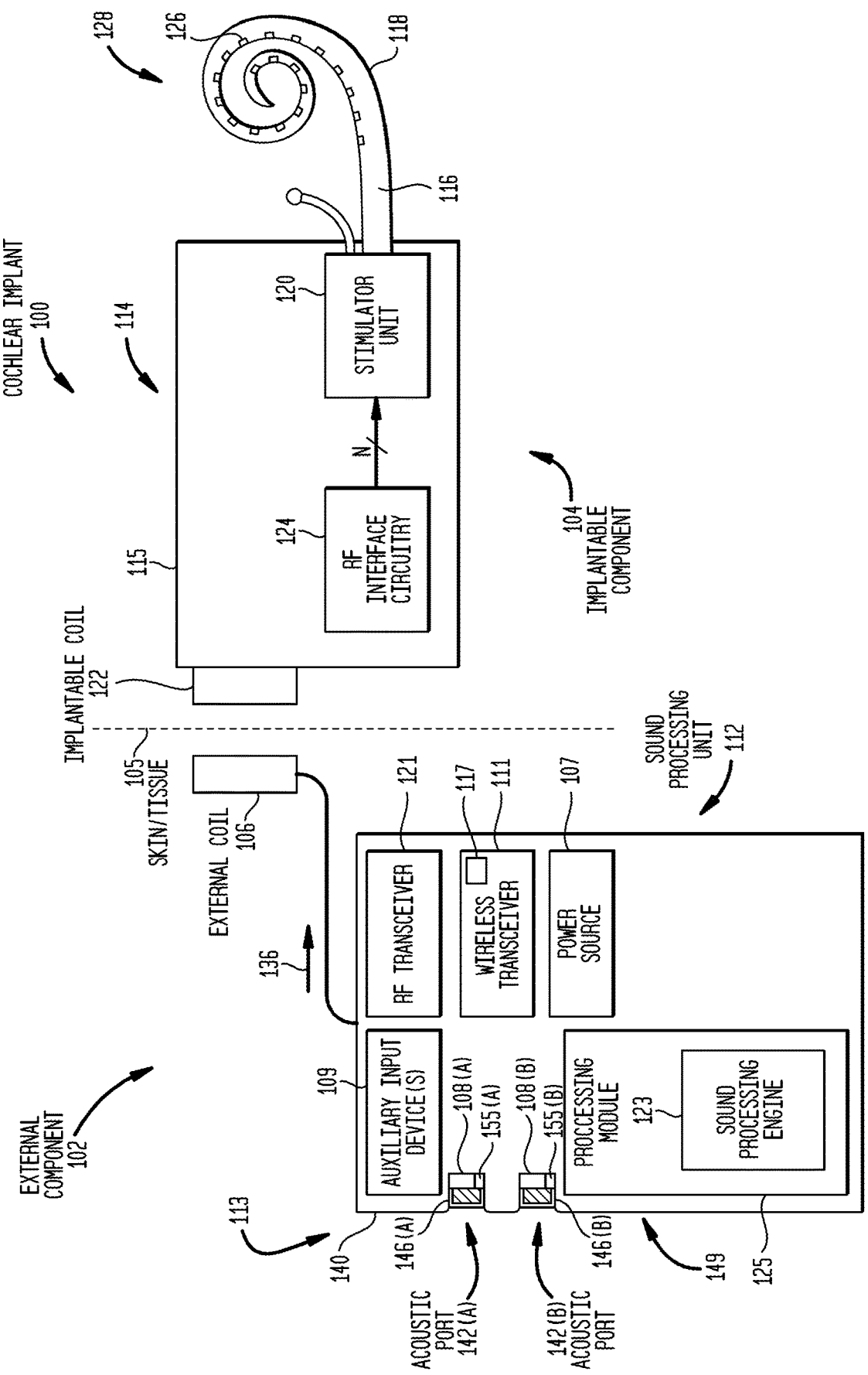
FIG. 1B is a simplified block diagram of the cochlear implant of FIG. 1A, in accordance with certain embodiments presented herein.

FIGS. 1A and 1B illustrate an exemplary cochlear implant 100 that includes two sub-surface indicator lights (indicator lights) 155(A) and 155(B), in accordance with certain embodiments presented herein. In this embodiment, the indicator lights are light-emitting diodes (LEDs) and, as such, are referred to as sub-surface LEDs 155(A) and 155(B). FIG. 1A is a schematic diagram of the exemplary cochlear implant 100, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is configured to be directly or indirectly attached to the body of the recipient and typically comprises an external coil 106 and, generally, a magnet (not shown in FIG. 1A) fixed relative to the external coil 106. The external component 102 also comprises one or more sound input elements/devices 113 for receiving sound signals at a sound processing unit (sound processor) 112. In this example, the one or more sound input devices 113 include microphones 108(A) and 108(B) each configured to capture/receive acoustic signals, one or more auxiliary input devices 109 (e.g., audio ports, such as a Direct Audio Input (DAI), data ports, such as a Universal Serial Bus (USB) port, cable port, etc.) configured to receive, and a wireless transmitter/receiver (transceiver) 111, each located in, on, or near the sound processing unit 112. The one or more auxiliary input devices 109 and the wireless transceiver 111 are configured to receive electrical signals that include sound data. As such, received sound signals may include acoustic signals, electrical signals that include sound data, etc. It is also to be appreciated that the sound processing unit 112 could also include other types of input devices 113, such as telecoils, which for ease of illustration have been omitted from FIGS. 1A and 1B.

The sound processing unit 112 includes a housing 140 that includes acoustic ports/openings 142(A) and 142(B) which allow acoustic sounds to enter the housing. The microphones 108(A) and 108(B) are positioned within the housing 140 proximate to the acoustic ports 142(A) and 142(B), respectively, so as to detect the acoustic sound signals entering through the acoustic ports 142. Also disposed on the housing 140 of the sound processing unit 112 is, for example, at least one power source (e.g., battery) 107, a radio-frequency (RF) transceiver 121, and a processing module 125 that includes a sound processing engine 123. The processing module 125, and thus the sound processing engine 123, may be formed by any of, or a combination of, one or more processors (e.g., one or more Digital Signal Processors (DSPs), one or more uC cores, etc.), firmware, software, etc. arranged to perform operations described herein. That is, the processing module 125 may be implemented on a printed circuit board (PCB) or some other arrangement.

In the examples of FIGS. 1A and 1B, the external component 102 comprises a behind-the-ear (BTE) sound processing unit 112 and a separate coil 106. As such, the housing 140 is configured (i.e., shaped, dimensioned, etc.) to be attached to, and worn adjacent to, the recipient's ear. However, it is to be appreciated that embodiments of the present invention may be implemented with systems that include other arrangements, such as systems comprising an off-the-ear (OTE) sound processing unit (i.e., a component which is configured to be magnetically coupled to the recipient's head and which includes an integrated coil), a mini or micro-BTE unit, an in-the-canal unit that is configured to be located in the recipient's ear canal, a body-worn sound processing unit, etc.

Returning to the example embodiment of FIGS. 1A and 1B, the implantable component 104 comprises an implant body (main module) 114, a lead region 116, and an intra-cochlear stimulating assembly 118, all configured to be implanted under the skin/tissue (tissue) 105 of the recipient. The implant body 114 generally comprises a hermetically-sealed housing 115 in which RF interface circuitry 124 and a stimulator unit 120 are disposed. The implant body 114 also includes an internal/implantable coil 122 that is generally external to the housing 115, but which is connected to the RF interface circuitry 124 via a hermetic feedthrough (not shown in FIG. 1B).

Stimulating assembly 118 is configured to be at least partially implanted in the recipient's cochlea 137. Stimulating assembly 118 includes a plurality of longitudinally spaced intra-cochlear electrical stimulating contacts (electrodes) 126 that collectively form a contact or electrode array 128 for delivery of electrical stimulation (current) to the recipient's cochlea. Stimulating assembly 118 extends through an opening in the recipient's cochlea (e.g., cochleostomy, the round window, etc.) and has a proximal end connected to stimulator unit 120 via lead region 116 and a hermetic feedthrough (not shown in FIG. 1B). Lead region 116 includes a plurality of conductors (wires) that electrically couple the electrodes 126 to the stimulator unit 120.

As noted, the cochlear implant 100 includes the external coil 106 and the implantable coil 122. The coils 106 and 122 are typically wire antenna coils each comprised of multiple turns of electrically insulated single-strand or multi-strand platinum or gold wire. Generally, a magnet is fixed relative to each of the external coil 106 and the implantable coil 122. The magnets fixed relative to the external coil 106 and the implantable coil 122 facilitate the operational alignment of the external coil with the implantable coil. This operational alignment of the coils 106 and 122 enables the external component 102 to transmit data, as well as possibly power, to the implantable component 104 via a closely-coupled wireless link formed between the external coil 106 with the implantable coil 122. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIG. 1B illustrates only one example arrangement.

The processing module 125 of sound processing unit 112 is configured to convert sound/audio signals received/captured at one or more of the input elements/devices 113 into stimulation control signals 136 for use in stimulating a first ear of a recipient (i.e., the sound processing engine 123 is configured to perform sound processing on input audio signals received at the sound processing unit 112). In the embodiment of FIG. 1B, the stimulation control signals 136 are provided to the RF transceiver 121, which transcutaneously transfers the stimulation control signals 136 (e.g., in an encoded manner) to the implantable component 104 via external coil 106 and implantable coil 122. That is, the stimulation control signals 136 are received at the RF interface circuitry 124 via implantable coil 122 and provided to the stimulator unit 120. The stimulator unit 120 is configured to utilize the stimulation control signals 136 to generate electrical stimulation signals (e.g., current signals) for delivery to the recipient's cochlea via one or more stimulating contacts 126. In this way, cochlear implant 100 electrically stimulates the recipient's auditory nerve cells, bypassing absent or defective hair cells that normally transduce acoustic vibrations into neural activity, in a manner that causes the recipient to perceive one or more components of the input audio signals.

In cochlear implants and other medical devices, there is often a need to convey information to the device recipient or another user. As such, it is typical for the external component of such medical devices to include one or more indicator lights (visual indicators) that can emit light in one or more manners so as to convey the desired information to the recipient or other user. For example, a typical sound processing unit for an auditory prosthesis (e.g., a BTE sound processing unit, an OTE sound processing unit, etc.) includes one or more indicator lights disposed at the external surface of the sound processing unit housing. In these conventional arrangements, the microphones and the indicator lights are separated from one another so that the microphones (i.e., the associated acoustic ports) and the indicator lights occupy separate areas of the outer surface of the sound processing unit housing. The indicator lights also generally use a somewhat geometrically defined radiant form or shape to make the emitted light visible from multiple directions/angles.

The separation of the indicator lights and microphones is due, at least in part, to several design constraints. First, since the indicator lights are located at the outer surface, they occupy some physical space, while the acoustic (microphone) ports also occupy some different physical space. Second, any more importantly, conventional microphones and conventional indicator lights are mounted on separate printed circuit boards (PCBs) within the sound processing unit. The result is a savings in two-dimensional surface space on the housing of the sound processing unit.

There is an increasing desire to shrink the size of medical device external components. However, the requirement that the microphones and the indicator lights be mounted on separate PCBs and each occupy different of the outer surface of the housing limits the size and flexibility in designing medical device external components. Additionally the requirement that the indicator light(s) and microphones be mounted on their own PCBs increases the physical space/volume required by the sound processing unit. As detailed above, the embodiments presented herein eliminate the requirement for this extra space, and allow for the manufacture of a more discrete/space efficient sound processing unit.

More specifically, embodiments presented herein address these and other issues through the use of sub-surface microphones which enable the design of a more space efficient sound processing unit (e.g., saving surface space on the housing), without compromising function.

In particular, as described in greater detail below, the use of sub-surface indicator light is enabled, at least in part, the use of microelectromechanical systems (MEMS) microphone technology and the presented herein arrangements are not particularly viable using conventional microphones. For example, the arrangement of conventional (e.g., Electret) microphones is such that they cause associated PCBs to be located relatively further from the external surface of the sound processor (i.e., between the microphone and the external surface of the sound processing unit). The reasons for this separation is that conventional (e.g., Electret) microphones cannot be reflow soldered, and therefore generally are not able to mounted on a PCB in a solid enough manner to use in mechanical fixation. Therefore, with Electret microphones, the microphones mechanical shape is used for retention of the microphone within a housing. In such arrangements, the PCB is on the back or side of the microphone (i.e., not between the between the microphone and the housing).

However, MEMS microphones employ a more advantageous architecture that allow associated PCBs to be located closer to the external surface of the sound processing unit. That is, MEMS microphones are specifically designed to be rigidly mounted on rigid PCBs, and come with suggested applications for such embodiments. In such arrangements, the acoustic pathway passes through the PCB (i.e., the PCB has to be between the mic and the housing). As such, with MEMS microphones, the PCB is placed close to the housing, which is not the case once with conventional (e.g., Electret) microphones. Consequently, the arrangements presented herein leverage this and mount the indicator light(s) on the same PCB as the MEMS microphone (i.e., the fact that a PCB needs to be near the interior surface of the housing is leveraged so that the PCB can then be used both to mount the microphone and the LED(s)).

Although closer to the surface than conventional microphone arrangements, the PCBs for the MEMS microphones are still within the housing. As a result, the indicator light(s) mounted on the same PCB as the MEMS microphone are positioned below the surface of the device housing, rather than actually on the outer surface of the housing, as is the case in conventional arrangements. In other words, by mounting the indicator lights on the same PCB as the MEMS microphone, the arrangements presented herein run counter to conventional requirements where the indicator lights must be located at the surface of the housing. The arrangements presented herein address this issue by employing optical connectors (e.g., light guides, light pipes, light diffusers, etc.) to optically couple the sub-surface indicator light(s) to the surface of the housing, thereby enabling the indicator light(s) to be visible from outside of the housing and, accordingly, provide their illuminating function.

Techniques presented herein are primarily described with reference to MEMS microphones. However, it is to be appreciated that the techniques presented herein may also be implemented with any other suitable microphone technology now know or later developed that possesses traits similar to those of MEMS microphones that enable the disclosed configuration (e.g., an architecture that allows associated PCBs to be located closer to the external surface of the housing, an architecture in which the microphones are specifically designed to be rigidly mounted on rigid PCBs, etc.).

Returning to the arrangement of FIGS. 1A and 1B, as noted above the sound processing unit 112 includes sub-surface LEDs 155(A) and 155(B). The LEDs 155(A) and 155(B) are referred to herein as "sub-surface" LEDs 155(A) and 155(B) because, unlike conventional arrangements, the LEDs 155(A) and 155(B) are not disposed at the outer surface 149 of the housing 140, but instead are positioned within the housing 140 (i.e., underneath/below the outer surface of the housing).

As shown in FIG. 1B, the sub-surface LEDs 155(A) and 155(B) are co-located with microphones 108(A) and 108(B), respectively. Microphones 108(A) and 108(B) are each microelectromechanical systems (MEMS) microphones and, in this arrangement, the LEDs 155(A) and 155(B) and the microphones 108(A) and 108(B) are mounted on the same printed circuit board (PCB) (not shown in FIG. 1B).

Since, as noted, the sub-surface LEDs 155(A) and 155(B) are positioned within the housing 140, the light emitted thereby may not be directly visible from outside the housing, only visible from very small angles, and/or only visible from certain directions. As such, the LEDs 155(A) and 155(B) are optically coupled to the outer surface 149 via optical connectors 146(A) and 146(B), respectively. That is, the optical connectors 146(A) and 146(B) are positioned between the sub-surface LEDs 155(A) and 155(B) to the external surface 149 and provide a path for light from the sub-surface LEDs 155(A) and 155(B) to the external surface 149.

In general, optical connectors in accordance with examples presented herein, such as optical connectors 146(A) and 146(B), are formed from a translucent (e.g., clear) material and are optimized at the internal surface thereof to gather the light emitted by the sub-surface LEDs and to transport the light to the surface of the device housing. In certain examples, the internal surfaces of the optical connectors are placed in contact with the sub-surface LEDs. The optical connectors in accordance with examples presented herein may also have minimal length, minimal angularity (e.g., straight shape), and/or polished faces. In one example, the optical connectors are formed from an optically clear polymer, such as polycarbonate (PC) or acrylic (PMMA).

Figure 2:
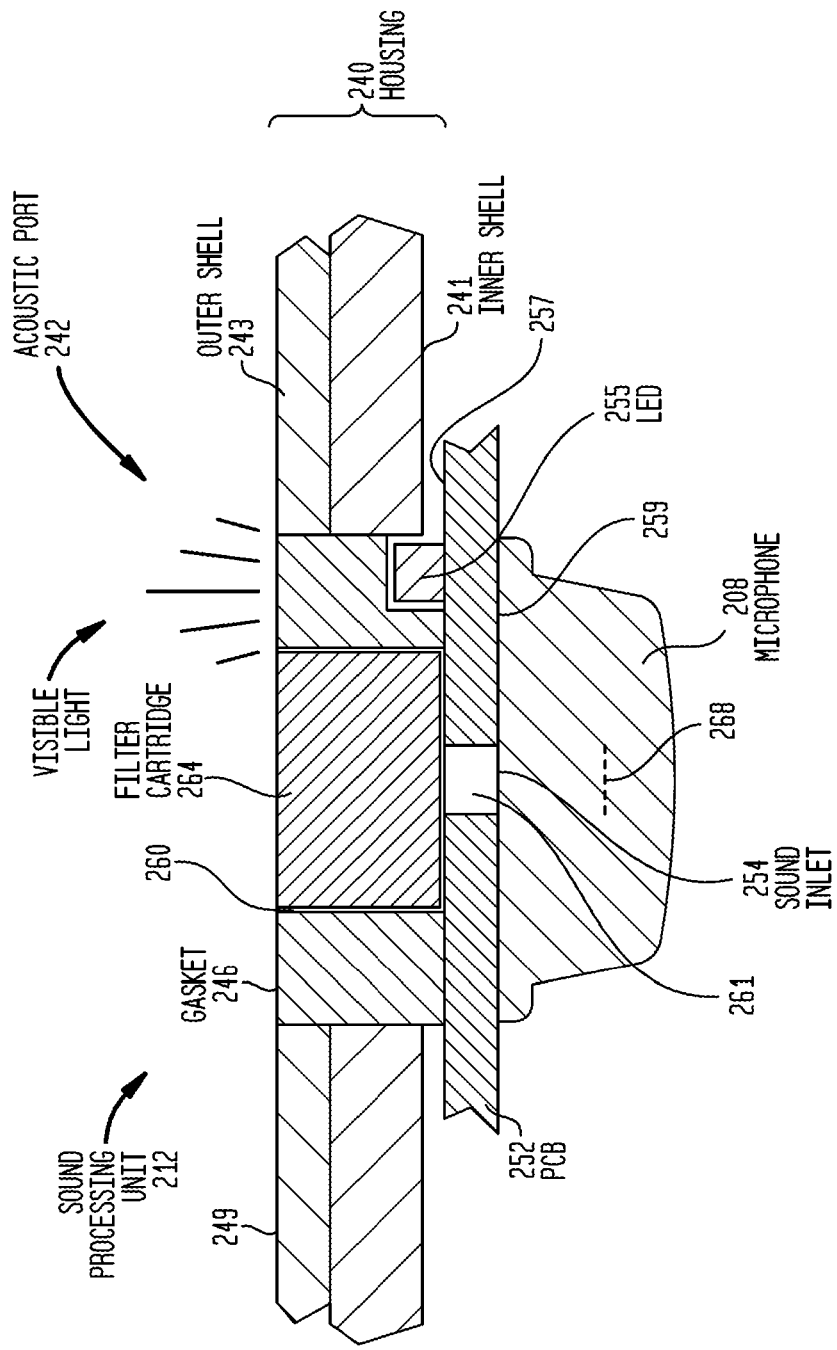
FIG. 2 is a cross-sectional view of a portion of a sound processing unit, in accordance with certain embodiments presented herein.

Further details of different example arrangements of sub-surface indicator lights and optical connectors are provided below. More specifically, referring first to FIG. 2, shown is a cross-sectional view of a portion of a sound processing unit 212 in accordance with certain embodiments presented herein. The sound processing unit 212 comprises a housing 240 which, in this example, is formed by two layers, namely a structural inner shell 241 and a decorative outer shell 243. It is to be appreciated that the use of a two-layer housing is illustrative and that other embodiments may include a single layer housing.

The illustrated portion of housing 240 (e.g., inner shell 241 and outer shell 243) includes an acoustic port 242, which allows acoustic sounds to enter the interior of the housing. Microphone 208 is positioned within the housing 240 proximate to the acoustic port 242 so as to detect the acoustic sound signals entering through the acoustic port. In the example of FIG. 2, the microphone 208 is a MEMS microphone mounted on a printed circuit board (PCB) 252. The microphone 208 includes a sound inlet 254 aligned with the acoustic port 242, as well as an acoustic membrane 268.

In operation, the acoustic sound signals (sound waves) entering the sound inlet 254 cause movement (vibration) of acoustic membrane 268 disposed in the microphone 208. The microphone 208 includes components that are configured to convert the movement of the acoustic membrane 268 into electrical microphone signals that represent the acoustic sound signals impinging on the acoustic membranes.

The microphone 208 is electrically connected to an electrical circuit and is configured to provide the electrical microphone signals to this electrical circuit. In the examples of FIG. 2, the electrical circuit is implemented on the PCB 252. The sound processing unit 212 may also include other components that, for ease of illustration, have been omitted from FIG. 2.

FIG. 2 also illustrates that a sub-surface indicator light (sub-surface visual indicator) 255 is co-located with the microphone 208. That is, the sub-surface indicator light 255 is also mounted on the PCB 252 (i.e., both the sub-surface indicator light 255 and the microphone 208 are mounted on the same PCB 252). In the arrangement of FIG. 2, sub-surface indicator light 255 is mounted on a first surface 257 of the PCB, while the microphone 208 is mounted on a second surface 259 of the PCB. However, it is to be appreciated that embodiments presented herein may include other arrangements of the microphone 208 and sub-surface indicator light 255.

In the example of FIG. 2, the sub-surface indicator light 255 is an light-emitting diode (LED) and, as such, is sometimes referred to herein as sub-surface LED 255. The sub-surface LED 255 may be a single color or multi-color sub-surface LED. In addition, although FIG. 2 illustrates an example that includes an LED, it is to be appreciated that embodiments presented herein may be implemented with other types of indicator lights.

As noted, the sub-surface LED 255 is located within the housing 240 (i.e., below/underneath outer surface 249 of the outer shell 243). As such, the light emitted by the sub-surface LED 255 may not be directly visible from outside the housing 240, only visible from very small angles, and/or only visible from certain directions. As such, the LED 255 is optically coupled to the outer surface 249 of outer shell 243 via an optical connector 246. That is, the optical connector 246 is positioned between the sub-surface LED 255 and the external surface 249 and provides a path for light from the sub-surface LED 255 to reach the external surface 249. In certain embodiments, the sub-surface LED 255 is in direct contact with the optical connector 246.

In FIG. 2, the optical connector 246 is also a microphone sealing gasket (microphone gasket) associated with the microphone 208. The microphone gasket 246 provides mechanical support for the microphone 208, mechanically isolates the microphone from vibrations delivered to the housing 240 (e.g., dampens and/or absorbs vibrations), and creates an acoustic seal between the microphone and the housing (e.g., prevents sound signals from passing between the microphone and the housing). The microphone gasket 246 may have, for example, a cylindrical shape that extends circumferentially about the inner surface of the acoustic port 242 (i.e., gasket lines the inner surface of the acoustic port). Additionally, the microphone gasket 246 is formed from a resiliently flexible material (e.g., silicone, rubber, etc.) and, as shown in FIG. 2, is attached to internal shell 241 of the housing 240 and the PCB 252. In certain examples, the microphone gasket 246 may be overmolded onto the housing 240, attached to the housing via adhesive, etc. Similar or other mechanisms may be used to attach the microphone gasket 246 to the PCB 252.

In this example, the microphone gasket 246 defines a cylindrical cavity 260 disposed in-line with the acoustic port 242. Disposed in the cavity 260 is a filter cartridge 264. The filter cartridge 264 covers the sound inlet 254 of the microphone 208 and prevents dirt, dust, and other debris from entering the sound inlet. The filter cartridge 264 is sometimes referred to herein as being acoustically transparent (e.g., penetrable by sound waves/energy without altering frequency response). In certain embodiments, the microphone gasket 246 is configured to compress the filter cartridge 264 to retain the filter cartridge in the cylindrical cavity 260 (e.g., press fit). In other embodiments, the filter cartridge 264 may be directly attached to the outer shell 243. It is also to be appreciated that the microphone gasket 246, filter cartridge 264, or both could be pliable in order to form a press fit or a form fit.

Also shown in FIG. 2, the microphone gasket 246 is attached to the first surface 257 of the PCB 252. The microphone 208 is directly mechanically coupled to (e.g., directly attached to) the second surface 259 of the PCB 252. In certain embodiments, the microphone 208 could be soldered to the PCB 252 (with a hole/opening 261 in the PCB allowing an acoustic path through the PCB to the sound inlet 254 of the microphone).

As noted above, in addition to retaining the filter cartridge 264, the microphone gasket 246 also functions as an optical connector for light emitted by sub-surface LED 255. In other words, the microphone gasket 246 is a translucent element that will illuminate in response to illumination of the sub-surface LED 255 and/or transport the light emitted by the sub-surface LED 255 to the outer surface 249 of the housing. As such, the optical properties of the microphone gasket 246 ensure that the light emitted by the sub-surface LED 255 will be visible outside of the housing 240 via the acoustic port 242. Stated differently, the LED 255 is optically coupled to the acoustic port via the microphone gasket 246.

FIG. 2 has been described with reference to a cylindrically shaped microphone gasket. However, it is to be appreciated that the microphone gasket may alternatively have any of a number of other shapes (e.g., oval, square, etc.). The microphone gasket 246 may also have any of a number of different colors or configurations that enable light from the sub-surface LED 255 to reach the outer surface 249 of the outer shell 243 (e.g., the dye or color of the gasket could cause it to light up a certain color).

Additionally, in alternative embodiments, the microphone gasket 246 may be replaced by a microphone mount that is formed from a rigid or semi-rigid material. In such embodiments, the microphone mount, although shaped similar to the microphone gasket, may be used to retain the microphone 208 in a desired position, but may provide little or no vibration isolation.

In still other embodiments, the microphone gasket 246 may be formed by a combination of resiliently flexible and rigid materials. For example, the microphone gasket 246 may be largely formed by a resiliently flexible material, but also includes rigid light guides embedded therein to transport light from LED 255 to the outer surface 249 of housing 240.

FIG. 2 has also been described with reference to a single sub-surface LED 255 positioned adjacent to the microphone gasket 246. It is to be appreciated that, in other embodiments, multiple LEDs may be positioned adjacent to the microphone gasket 246.

In summary, FIG. 2 illustrates an embodiment in which a microphone gasket is disposed between a sub-surface LED and the outer surface of the housing. The microphone gasket, in addition to being formed from a substantially flexible material configured to mechanically isolate the microphone from vibrations delivered to the housing and to create an acoustic seal between the microphone and the housing, has associated optical properties so as to provide a path for light emitted from the sub-surface LED to reach the outer surface of the housing (i.e., the LED is optically coupled to the acoustic port via the microphone gasket such that light emitted from the at least one indicator light is visible outside of the housing via the acoustic port). Additionally, the MEMS microphone is co-located with the LED (i.e., the MEMS microphone and the LED(s) are mounted on the same PCB). Furthermore, FIG. 2 illustrates an arrangement in which the sub-surface LED forms part of the sound canal (i.e., is disposed in the acoustic port in the pathway of incoming sound signals).

Figure 3:
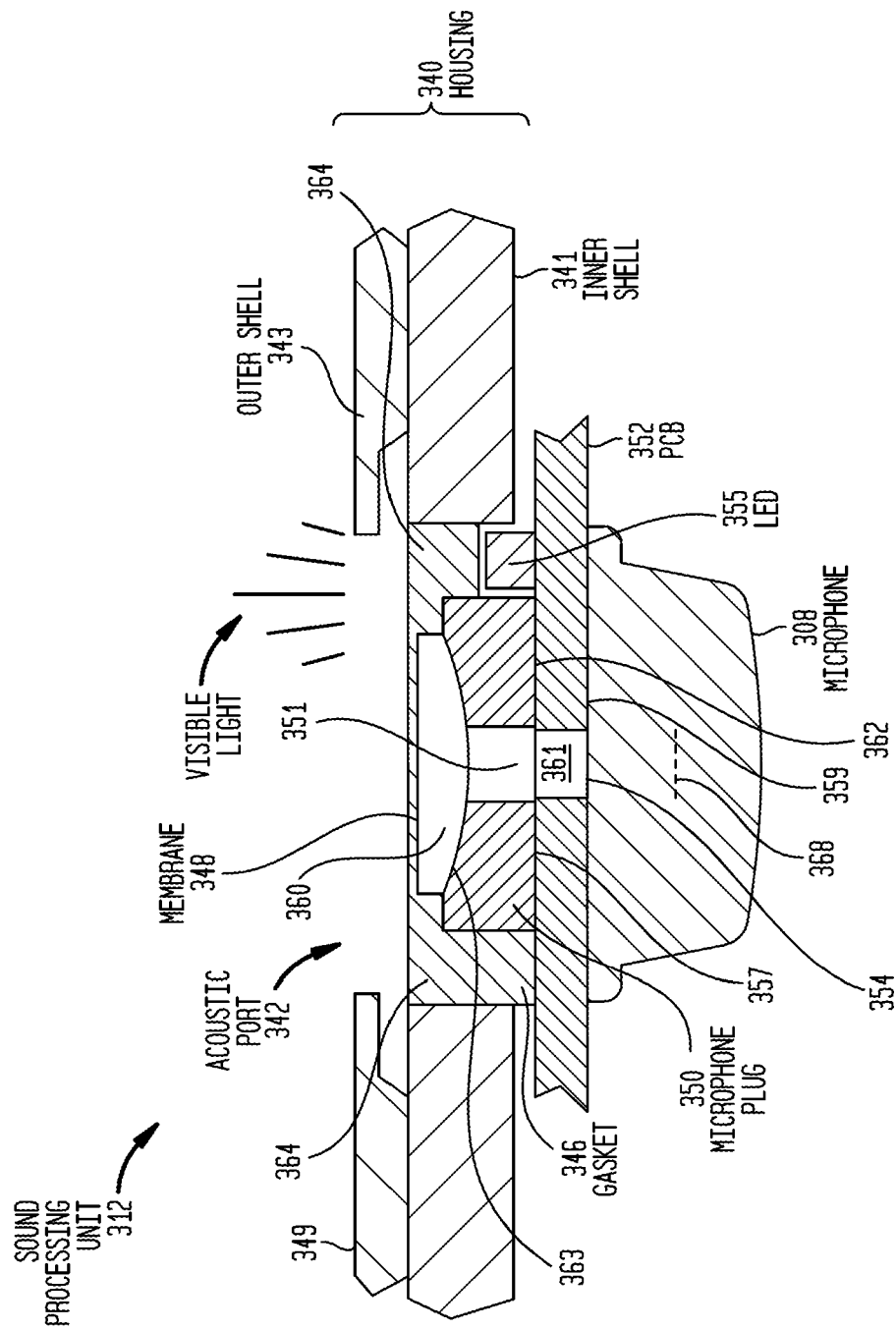
FIG. 3 is a cross-sectional view of a portion of a sound processing unit, in accordance with certain embodiments presented herein.

Referring next to FIG. 3, shown is a cross-sectional view of a portion of a sound processing unit 312 in accordance with certain embodiments presented herein. The sound processing unit 312 comprises a housing 340 which, in this example, is formed by two layers, namely a structural inner shell 341 and a decorative outer shell 343. It is to be appreciated that the use of a two-layer housing is illustrative and that other embodiments may include a single layer housing.

The illustrated portion of housing 340 (e.g., inner shell 341 and outer shell 343) includes an acoustic port 342, which allows acoustic sounds to enter the interior of the housing. Microphone 308 is positioned within the housing 340 proximate to the acoustic port 342 so as to detect the acoustic sound signals entering through the acoustic port. In the example of FIG. 3, the microphone 308 is a MEMS microphone mounted on a printed circuit board (PCB) 352. The microphone 308 includes a sound inlet 354 aligned with the acoustic port 342, as well as an acoustic membrane 368.

In operation, the acoustic sound signals (sound waves) entering the sound inlet 354 cause movement (vibration) of acoustic membrane 368 disposed in the microphone 308. The microphone 308 includes components that are configured to convert the movement of the acoustic membrane 368 into electrical microphone signals that represent the acoustic sound signals impinging on the acoustic membranes.

The microphone 308 is electrically connected to an electrical circuit and is configured to provide the electrical microphone signals to this electrical circuit. In the examples of FIG. 3, the electrical circuit is implemented on the PCB 352. The sound processing unit 312 may also include other components that, for ease of illustration, have been omitted from FIG. 3.

FIG. 3 also illustrates that a sub-surface indicator light 355 is co-located with the microphone 308. In FIG. 3, the sub-surface indicator light 355 is a single color or multi-color sub-surface LED that is co-located with the microphone 308 on the PCB 352 (i.e., both the LED 355 and the microphone 308 are mounted on the same PCB 352). In particular, sub-surface LED 355 is mounted on a first surface 357 of the PCB, while the microphone 308 is mounted on a second surface 359 of the PCB. However, it is to be appreciated that embodiments presented herein may include other arrangements of the microphone 308 and sub-surface LED 355. In addition, although FIG. 3 illustrates an example that includes a sub-surface LED, it is to be appreciated that embodiments presented herein may be implemented with other types of indicator lights.

As noted, the sub-surface LED 355 is located within the housing 340 (i.e., below/underneath outer surface 349 of the outer shell 343). As such, the light emitted by the sub-surface LED 355 may not be directly visible from outside the housing 340, only visible from very small angles, and/or only visible from certain directions. As such, the LED 355 is optically coupled to the outer surface 349 of outer shell 343 via an optical connector 346. That is, the optical connector 346 is positioned between the sub-surface LED 355 and the external surface 349 and provides a path for light from the sub-surface LED 355 to reach the external surface 249. In certain embodiments, the sub-surface LED 355 is in direct contact with the optical connector 346.

In FIG. 3, the optical connector 346 is also a microphone gasket associated with the microphone 308. The microphone gasket 346 provides mechanical support for the microphone 308, mechanically isolates the microphone from vibrations delivered to the housing 340, and creates an acoustic seal between the microphone and the housing. The microphone gasket 346 may have, for example, a cylindrical shape that defines a cylindrical interior cavity 360 disposed in-line with the acoustic port 342. Additionally, the microphone gasket 346 is formed from a resiliently flexible material (e.g., silicone, rubber, etc.) and, as shown in FIG. 3, is attached to internal shell 341 of the housing 340. In certain examples, the microphone gasket 346 may be overmolded onto the housing 340.

As shown in FIG. 3, a membrane 348 is disposed between the interior cavity 360 of the microphone gasket 346 and the acoustic port 342. The membrane 348 is sometimes referred to herein as being acoustically transparent (e.g., penetrable by sound waves/energy without altering frequency response) and contaminant-proof (e.g., impenetrable by water, dust, and other contaminants).

The membrane 348 is connected to the microphone gasket 346 to form an acoustic chamber with the interior cavity 360 of the microphone gasket. In the example of FIG. 3, the membrane 348 is integral/unitary with the microphone gasket 346 (e.g., the microphone gasket and the membrane are formed as a single component). However, it is to be appreciated that, in alternative embodiments, the membrane 348 and the microphone gasket 346 may be separate elements that are joined/connected together via, for example, adhesive, ultrasonically welding, etc.

Also shown in FIG. 3 is a microphone plug 350, which includes a first end 362, a second end 363, and through-hole 351. The through-hole 351 extends from the first end 362 to the second end 363). In addition, the first end 362 is directly mechanically coupled to (e.g., directly attached to) the first surface 357 of the PCB 352 adjacent to the sub-surface LED 355. As noted, the microphone 308 is directly mechanically coupled to (e.g., directly attached to) the second surface 359 of the PCB 352. In other words, in FIG. 3, the microphone plug 350 is indirectly coupled to the microphone 308 via PCB 352 such that the PCB 352 is located between the microphone plug 350 and the sound inlet 354.

In certain embodiments, the microphone 308 could be soldered to the PCB 352 (with a hole/opening 361 in the PCB allowing an acoustic path through the PCB to the sound inlet 354 of the microphone). The cylindrical plug 350 may be, for example, soldered, glued, soldered and glued, etc. to the PCB 352. The microphone plug 350 and microphone 308 can then be inserted into the microphone gasket 346.

In certain examples, the microphone plug 350 is formed from a material that is relatively more rigid than the resiliently flexible material of the microphone gasket 346. In addition, the interior cavity 360 has an inner dimension (e.g., inside diameter) between the sidewalls that is smaller than an outer dimension (e.g., outside diameter) of the microphone plug 350. As such, when the microphone plug 350 is inserted into the interior cavity 360 of the microphone gasket 346, the microphone plug 360 is configured to compress the sidewalls of the microphone gasket (i.e., the walls surrounding/defining the sides of the interior cavity 360). In certain embodiments, the compression of the sidewalls is sufficient to retain the microphone plug 350 within the microphone gasket 346. However, in other embodiments, the sidewalls of the cavity 360 and the microphone plug 360 may include corresponding interlocking features configured to releasably lock the microphone plug within the microphone gasket.

As noted above, in addition to retaining the microphone plug 350 (and the attached microphone 308), the microphone gasket 346 also functions as an optical connector for light emitted by sub-surface LED 355. In other words, the microphone gasket 346 is a translucent element that will illuminate in response to illumination of the sub-surface LED 355 and/or transport the light emitted by the sub-surface LED 355 to the outer surface 349 of the housing. As such, the optical properties of the microphone gasket 346 ensure that the light emitted by the sub-surface LED 355 will be visible outside of the housing 340 via the acoustic port 342. Stated differently, the LED 355 is optically coupled to the acoustic port via the microphone gasket 246.

FIG. 3 has been described with reference to a cylindrically shaped microphone gasket. However, it is to be appreciated that the microphone gasket may alternatively have any of a number of other shapes (e.g., oval, square, etc.). The microphone gasket 346 may also have any of a number of different colors or configurations that enable light from the sub-surface LED 355 to reach the outer surface 349 of the outer shell 343 (e.g., the dye or color of the gasket could cause it to light up a certain color).

Additionally, in alternative embodiments, the microphone gasket 346 may be replaced by a microphone mount that is formed from a rigid or semi-rigid material. In such embodiments, the microphone mount, although shaped similar to the microphone gasket, may be used to retain the microphone 308 in a desired position, but may provide little or no vibration isolation.

In still other embodiments, the microphone gasket 346 may be formed by a combination of resiliently flexible and rigid materials. For example, the microphone gasket 346 may be largely formed by a resiliently flexible material, but also includes rigid light guides embedded therein to transport light from LED 355 to the outer surface 349 of housing 340.

In summary, FIG. 3 illustrates an embodiment in which a microphone gasket is disposed between a sub-surface LED and the outer surface of the housing. The microphone gasket, in addition to formed from a substantially flexible material configured to mechanically isolate the microphone from vibrations delivered to the housing and to create an acoustic seal between the microphone and the housing, has associated optical properties so as to provide a path for light emitted from the sub-surface LED to reach the outer surface of the housing (i.e., the LED is optically coupled to the acoustic port via the microphone gasket such that light emitted from the at least one indicator light is visible outside of the housing via the acoustic port). Additionally, the MEMS microphone is co-located with the LED (i.e., the MEMS microphone and the LED(s) are mounted on the same PCB). Furthermore, FIG. 3 illustrates an arrangement in which the sub-surface LED forms part of the sound canal (i.e., is disposed in the acoustic port in the pathway of incoming sound signals).

Figure 4:
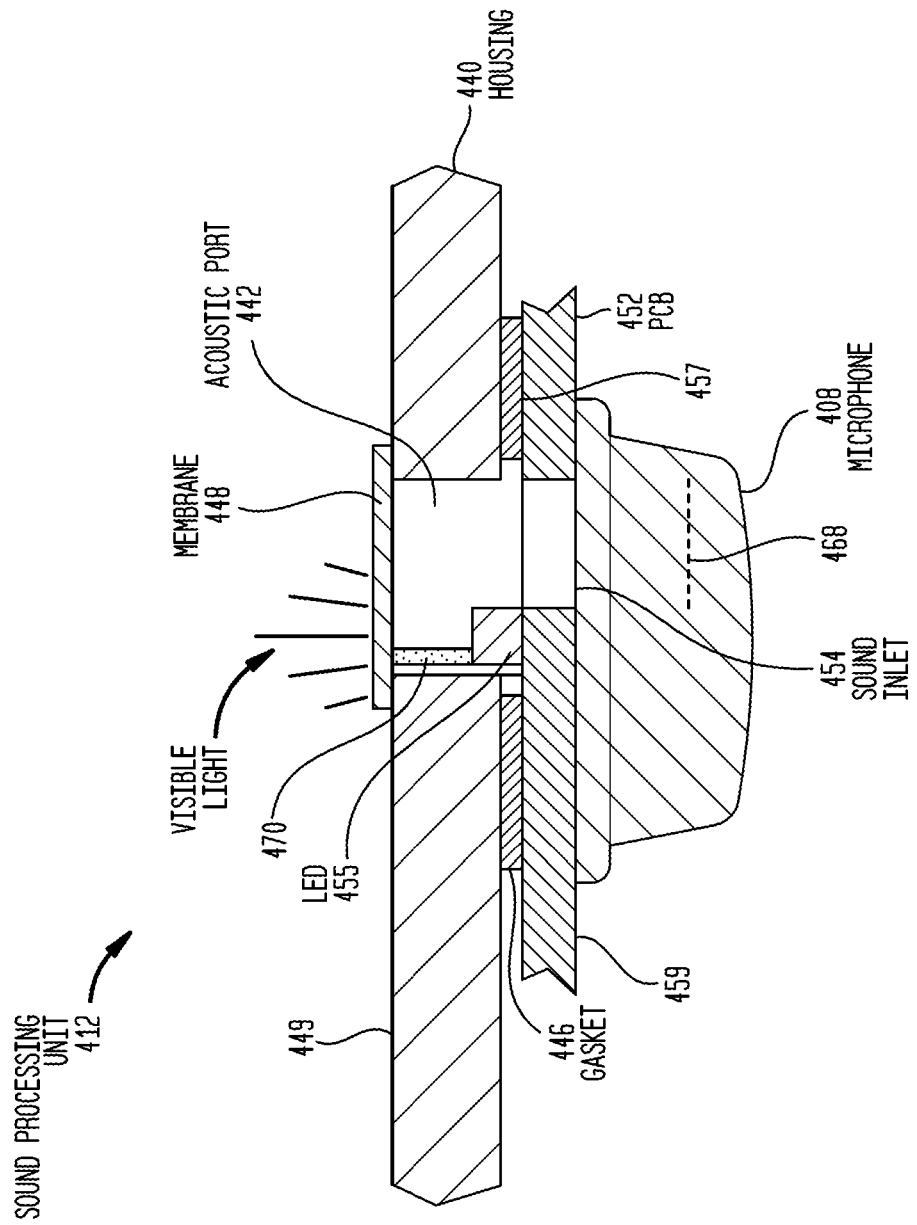
FIG. 4 is a cross-sectional view of a portion of a sound processing unit, in accordance with certain embodiments presented herein.

Shown in FIG. 4 is a cross-sectional view of a portion of a sound processing unit 412 in accordance with certain embodiments presented herein. The sound processing unit 412 comprises a housing 440, which include an outer surface 449 and an acoustic port 442. The acoustic port 442 allows acoustic sounds to enter the interior of the housing 440. As shown in FIG. 4, a membrane 448 is attached to the outer surface 449 of the housing 440 (e.g., via adhesive) and seals the acoustic port 442. The membrane 448 is sometimes referred to herein as being acoustically transparent (e.g., penetrable by sound waves/energy without altering frequency response) and contaminant-proof (e.g., impenetrable by water, dust, and other contaminants).

A microphone 408 is positioned within the housing 440 proximate to the acoustic port 442 so as to detect the acoustic sound signals entering through the acoustic port. In the example of FIG. 4, the microphone 408 is a MEMS microphone mounted on a printed circuit board (PCB) 452. The microphone 408 includes a sound inlet 454 aligned with the acoustic port 442, as well as an acoustic membrane 468.

In operation, the acoustic sound signals (sound waves) entering the sound inlet 454 cause movement (vibration) of acoustic membrane 468 disposed in the microphone 408. The microphone 408 includes components that are configured to convert the movement of the acoustic membrane 468 into electrical microphone signals that represent the acoustic sound signals impinging on the acoustic membranes. The microphone 408 is electrically connected to an electrical circuit and is configured to provide the electrical microphone signals to this electrical circuit. In the examples of FIG. 4, the electrical circuit is implemented on the PCB 452. The sound processing unit 412 may also include other components that, for ease of illustration, have been omitted from FIG. 4.

FIG. 4 also illustrates that a sub-surface indicator light 455 is co-located with the microphone 408. In FIG. 4, the sub-surface indicator light 455 is a single color or multi-color sub-surface LED that is also co-located with the MEMS microphone 408 on the PCB 452 (i.e., both the LED 455 and the microphone 408 are mounted on the same PCB 452). In particular, sub-surface LED 455 is mounted on a first surface 457 of the PCB, while the microphone 408 is mounted on a second surface 459 of the PCB. However, it is to be appreciated that embodiments presented herein may include other arrangements of the microphone 408 and sub-surface LED 455. In addition, although FIG. 4 illustrates an example that includes an LED, it is to be appreciated that embodiments presented herein may be implemented with other types of indicator lights.

As noted, the sub-surface LED 455 is located within the housing 440 (i.e., below/underneath outer surface 449). As such, the light emitted by the sub-surface LED 455 may not be directly visible from outside the housing 440, only visible from very small angles, and/or only visible from certain directions. However, in this example, the LED 455 is located within the acoustic port 442 and is optically coupled to the outer surface 449 via membrane 448. That is, the membrane 448 has optical properties so that it can function as an optical connector for light from the sub-surface LED 455 (i.e., transport light from the sub-surface LED 455 to the external surface 449). In certain embodiments, the sub-surface LED 455 is in direct contact with the membrane 448 or, as shown in FIG. 4, a second optical connector (e.g., light guide) 470 optically couples the LED 455 to the membrane 448. The membrane 448 is translucent (e.g., transparent).

Also shown in FIG. 4 is a microphone gasket 446 that provides mechanical support for the microphone 408 and creates an acoustic seal between the microphone and the housing 440. In certain embodiments, the microphone gasket 446 is formed from a flexible material (e.g., silicone, rubber, etc.) and also mechanically isolates the microphone from vibrations delivered to the housing 440.

The microphone gasket 446 may have, for example, a cylindrical shape that extends circumferentially a lower edge of the acoustic port 442. Additionally, the microphone gasket 446 is attached an inner surface of the housing 440 and the PCB 452. In certain examples, the microphone gasket 446 may be overmolded onto the housing 440, attached to the housing via adhesive, etc. Similar or other mechanisms may be used to attach the microphone gasket 446 to the PCB 452. In certain embodiments, the microphone gasket 446 is a sealing compound or flexible adhesive.

In summary, FIG. 4 illustrates an embodiment in which a sub-surface LED is positioned in an acoustic port of a device housing (i.e., is part of the sound canal). The sealing membrane covering the acoustic port has optical properties so that light emitted by the sub-surface LED is visible outside of the housing. That is, the sealing membrane, and optionally an optical component optically coupling the sub-surface LED to the membrane, provide a path for light emitted from the sub-surface LED to reach the outer surface of the housing.

Figure 5A:
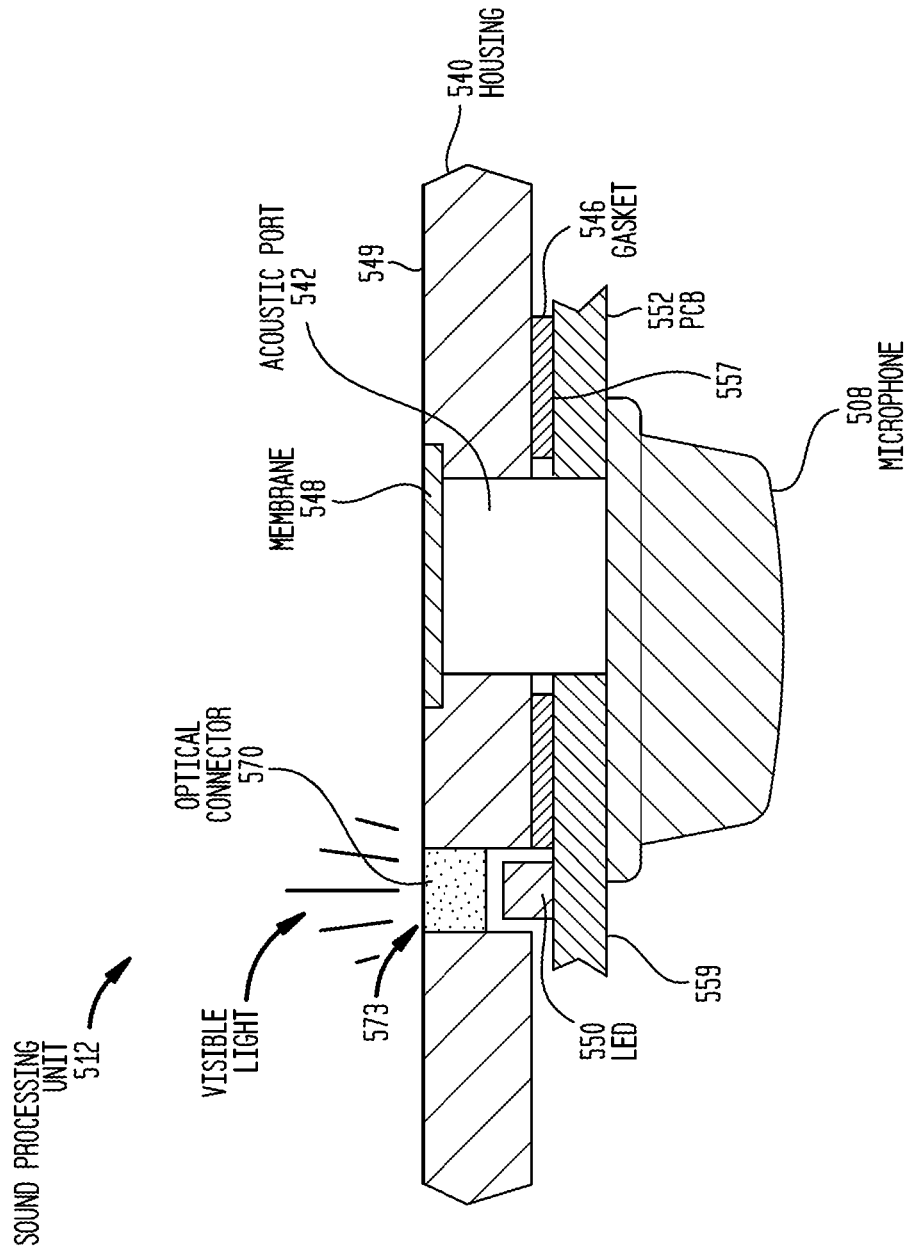
FIG. 5A is a cross-sectional view of a portion of a sound processing unit, in accordance with certain embodiments presented herein.

Shown in FIG. 5A is a cross-sectional view of a portion of a sound processing unit 512 in accordance with certain embodiments presented herein. The sound processing unit 512 comprises a housing 540, which includes an outer surface 549 and an acoustic port 542. The acoustic port 542 allows acoustic sounds to enter the interior of the housing 540. As shown in FIG. 5A, a membrane 548 is attached to the outer surface 549 of the housing 540 (e.g., via adhesive) and seals the acoustic port 542. The membrane 548 is sometimes referred to herein as being acoustically transparent (e.g., penetrable by sound waves/energy without altering frequency response) and contaminant-proof (e.g., impenetrable by water, dust, and other contaminants).

A microphone 508 is positioned within the housing 540 aligned with the acoustic port 542 so as to detect the acoustic sound signals entering through the acoustic port. In the example of FIG. 5A, the microphone 508 is a MEMS microphone mounted on a printed circuit board (PCB) 552. Similar to the microphones described elsewhere herein, microphone 508 is configured to convert sound signals entering the acoustic port 542 into electrical microphone signals that represent the acoustic sound signals. The microphone 508 is electrically connected to an electrical circuit and is configured to provide the electrical microphone signals to this electrical circuit. In the examples of FIG. 5A, the electrical circuit is implemented on the PCB 552. The sound processing unit 512 may also include other components that, for ease of illustration, have been omitted from FIG. 5A.

FIG. 5A also illustrates that the sound processing unit 512 includes a sub-surface indicator light 555. The sub-surface indicator light 555 is a single color or multi-color sub-surface LED which is co-located with the microphone 508 on the same PCB 552 (i.e., both the LED 555 and the microphone 508 are mounted on the same PCB 552). In particular, sub-surface LED 555 is mounted on a first surface 557 of the PCB, while the microphone 508 is mounted on a second surface 559 of the PCB. However, it is to be appreciated that embodiments presented herein may include other arrangements of the microphone 508 and sub-surface LED 555. In addition, although FIG. 5A illustrates an example that includes an LED, it is to be appreciated that embodiments presented herein may be implemented with other types of indicator lights.

As noted, the sub-surface LED 555 is located within the housing 540 (i.e., below/underneath outer surface 549). As such, the light emitted by the sub-surface LED 555 may not be directly visible from outside the housing 540, only visible from very small angles, and/or only visible from certain directions. However, in this example, the LED 555 is optically coupled to the outer surface 549 via an optical connector 570. That is, the optical connector 570 provides a path for light from the sub-surface LED 555 to reach the external surface 549. In certain embodiments, the sub-surface LED 555 is in direct contact with the optical connector 570. In this example, the optical connector 570 is disposed in a lighting port 573 of the housing 540.

Also shown in FIG. 5A is a microphone gasket 546 that provides mechanical support for the microphone 508 and creates an acoustic seal between the microphone and the housing 540. In certain embodiments, the microphone gasket 546 is formed from a flexible material (e.g., silicone, rubber, etc.) and also mechanically isolates the microphone from vibrations delivered to the housing 540.

The microphone gasket 546 may have, for example, a cylindrical shape that extends circumferentially a lower edge of the acoustic port 542. Additionally, the microphone gasket 546 is attached an inner surface of the housing 540 and the PCB 552. In certain examples, the microphone gasket 546 may be overmolded onto the housing 540, attached to the housing via adhesive, etc. Similar or other mechanisms may be used to attach the microphone gasket 546 to the PCB 552. In certain embodiments, the microphone gasket 546 is a sealing compound or flexible adhesive.

In summary, FIG. 5A illustrates an embodiment in which a sub-surface LED is co-located with a MEMS microphone on the same PCB. As a result, the acoustic port and the lighting port in the housing are positioned adjacent to one another. Additionally, an optical connector optically couples the sub-surface LED to the external surface of the housing so that light emitted by the sub-surface LED is visible outside of the housing via the lighting port.

Figure 5B:
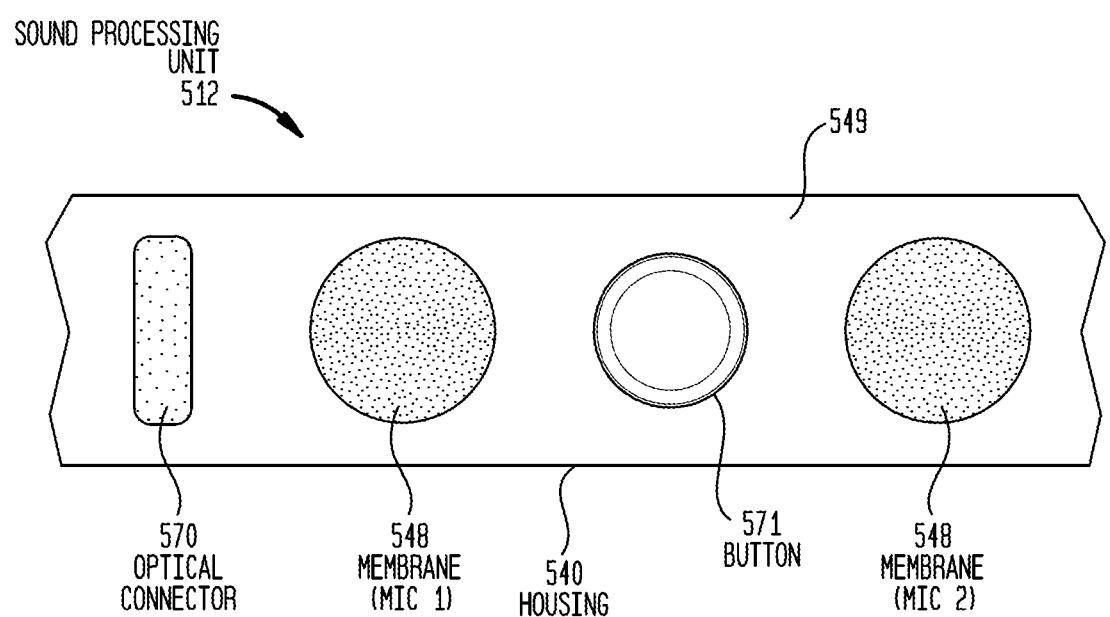
FIG. 5B is a top view of the portion of the sound processing unit of FIG. 5A, in accordance with certain embodiments presented herein.

FIG. 5B is a top view of a larger portion of the sound processing unit 512 of FIG. 5A. More specifically, FIG. 5B illustrates that the optical connector 570 is positioned adjacent to a first microphone membrane 548 (associated with a first microphone), a button 571, and a second microphone membrane 548 (associated with a second microphone). In general, the embodiment of FIG. 5B can be applied to one or more of the microphones of a sound processing unit or other device, thereby allowing indicator lights to be placed immediately besides the acoustic opening of the microphone(s).

Figure 6A:
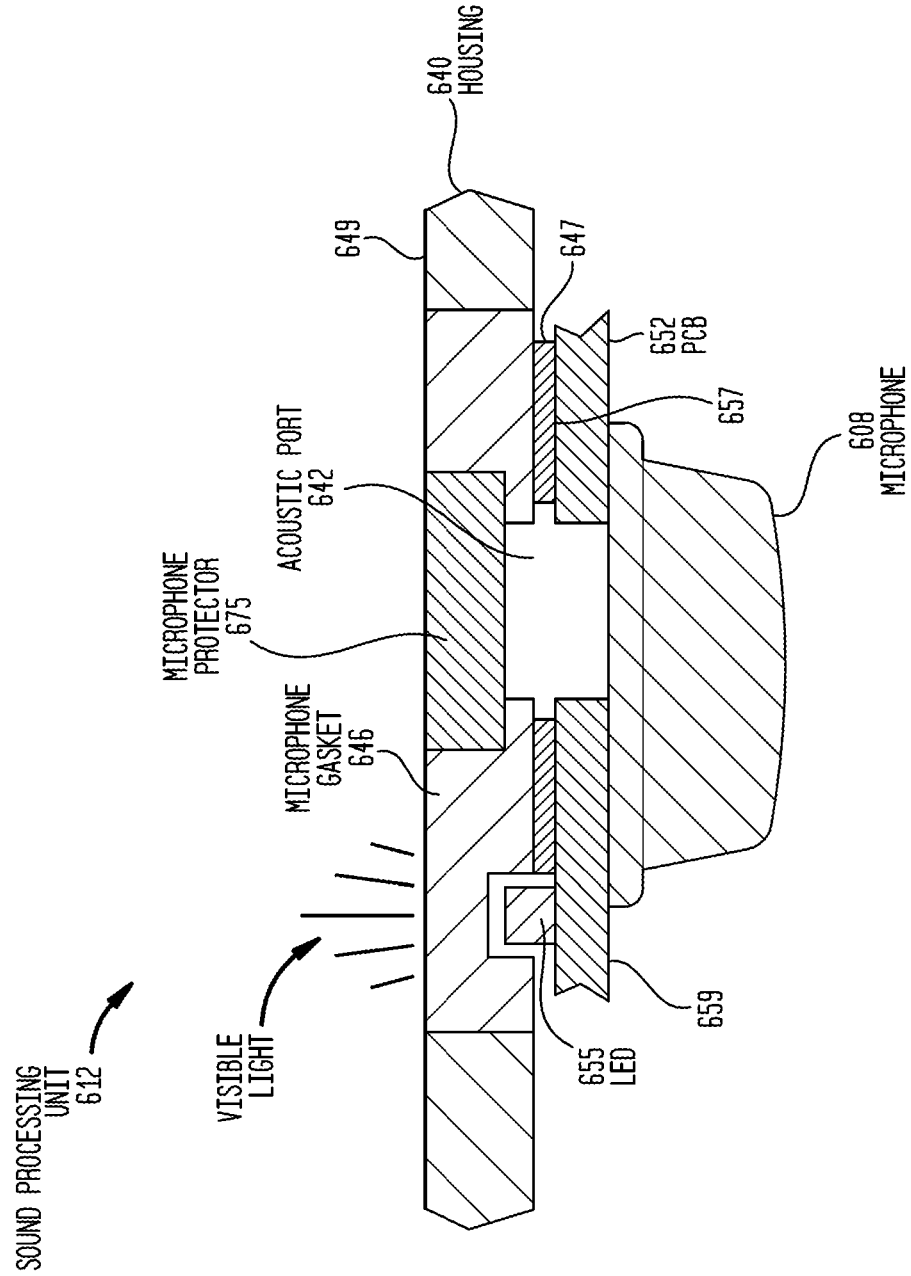
FIG. 6A is a cross-sectional view of a portion of a sound processing unit, in accordance with certain embodiments presented herein.
Figure 6B:
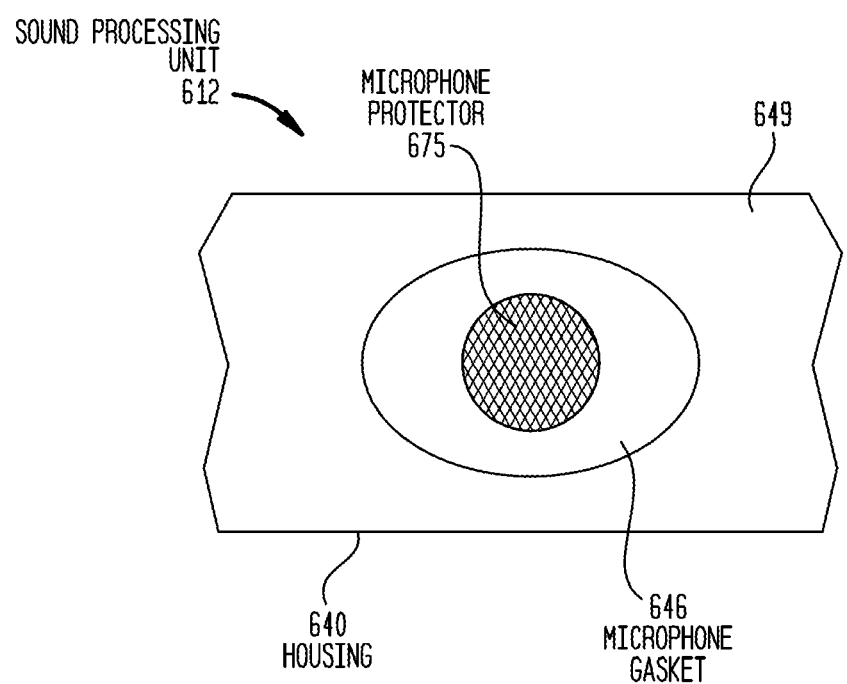
FIG. 6B is a top view of the portion of the sound processing unit of FIG. 6A, in accordance with certain embodiments presented herein.

FIGS. 6A and 6B illustrate an arrangement for another device, such as a sound processing unit, in accordance with embodiments presented herein. More specifically, FIG. 6A is a cross-sectional view of a portion of a sound processing unit 612, while FIG. 6B is a top view of the same portion of the sound processing unit 612.

The sound processing unit 612 comprises a housing 640, which includes an outer surface 649 and an acoustic port 642. The acoustic port 642 allows acoustic sounds to enter the interior of the housing 640. A microphone 608 is positioned within the housing 640 aligned with the acoustic port 642 so as to detect the acoustic sound signals entering through the acoustic port. In the example of FIG. 6, the microphone 608 is a MEMS microphone mounted on a printed circuit board (PCB) 652. Similar to the microphones described elsewhere herein, microphone 608 is configured to convert sound signals entering the acoustic port 642 into electrical microphone signals that represent the acoustic sound signals. The microphone 608 is electrically connected to an electrical circuit and is configured to provide the electrical microphone signals to this electrical circuit. In the examples of FIGS. 6A and 6B, the electrical circuit is implemented on the PCB 652. The sound processing unit 612 may also include other components that, for ease of illustration, have been omitted from FIGS. 6A and 6B.

As shown in FIGS. 6A and 6B, a microphone protector 675 (e.g., filter cartridge, membrane, etc.) is disposed between the outer surface 649 of the housing 640 and the microphone 608. The microphone protector 675 is acoustically transparent and protects the microphone 608 from ingress of dirt, dust, and/or other debris.

FIGS. 6A and 6B illustrate that the sound processing unit 612 includes a sub-surface indicator light 655. The sub-surface indicator light 655 is a single color or multi-color sub-surface LED which is co-located with the microphone 608 on the PCB 652 (i.e., both the LED 655 and the microphone 608 are mounted on the same PCB 652). In particular, sub-surface LED 655 is mounted on a first surface 657 of the PCB, while the microphone 608 is mounted on a second surface 659 of the PCB. However, it is to be appreciated that embodiments presented herein may include other arrangements of the microphone 608 and sub-surface LED 655. In addition, although FIGS. 6A and 6B illustrate an example that includes an LED, it is to be appreciated that embodiments presented herein may be implemented with other types of indicator lights.

As noted, the sub-surface LED 655 is located within the housing 640 (i.e., below/underneath outer surface 649). As such, the light emitted by the sub-surface LED 655 may not be directly visible from outside the housing 640, only visible from very small angles, and/or only visible from certain directions. However, in this example, the LED 655 is located within the acoustic port 642 and is optically coupled to the outer surface 649 via a microphone gasket 646. That is, the microphone gasket 646 is similar to the above arrangements and is formed from a translucent (e.g., transparent) material that provides a path for light from the sub-surface LED 655 to reach the external surface 649. In certain embodiments, the sub-surface LED 655 is in direct contact with the microphone gasket 646. Also shown in FIG. 6A is a secondary microphone gasket 647 that is disposed between the PCB and the gasket 646. In alternative embodiments, secondary microphone gasket 647 may be omitted and microphone gasket 646 may in direct contact with the PCB 652.

In the example of FIGS. 6A and 6B, the microphone gasket 646 is positioned in the optical port 642 and defines a cavity 660 in which the microphone protector 675 is located. In certain embodiments, the microphone protector 675 may be integral with, or attached to, the optical microphone gasket 646. Alternatively, the microphone protector 675 may be configured for an interference or friction fit with the microphone gasket 646. For example, the microphone gasket 646 may be configured (e.g. sized, dimensioned, etc.) to exert a compressive force on the microphone protector 675 when the microphone protector 675 is positioned in cavity 660. The microphone gasket 646 may be attached to the PCB 652 (e.g., using an adhesive) and provides mechanical support for the microphone 608 and creates an acoustic seal between the microphone and the housing 640. In certain embodiments, the microphone gasket 646 is formed from a flexible material (e.g., silicone, rubber, etc.) and also mechanically isolates the microphone from vibrations delivered to the housing 640.

In summary, FIGS. 6A and 6B illustrate an embodiment in which a sub-surface LED is co-located with a MEMS microphone on the same PCB. Addition, the sub-surface LED is located within the acoustic port and an optical housing insert (optical connector) optically couples the sub-surface LED to the external surface of the housing so that light emitted by the sub-surface LED is visible outside of the housing. In contrast to FIG. 2, in the embodiments of FIGS. 6A and 6B, the LED is located opposite the microphones solder pads, while in FIG. 2 the LED is not.

As detailed above, presented herein are arrangements for devices, such as sound processing units, that make use of sub-surface indicator lights. The arrangements presented herein are, at least in part, enabled by the use of MEMS microphone technology and the presented herein arrangements are not particularly viable using conventional microphones. MEMS microphones employ a more advantageous architecture that allow associated PCBs to be located closer to the external surface of the sound processing unit. Consequently, the arrangements presented herein leverage this and mount the indicator light(s) on the same PCB as the MEMS microphone. This is in contrast to conventional arrangements where the indicator light(s) are mounted on their own PCB.

However, although closer to the surface than conventional microphone arrangements, the PCBs for the MEMS microphones are still below the surface of the device housing. As a result, the indicator light(s) mounted on the same PCB as the MEMS microphone are also below the surface of the housing. In other words, by mounting the indicator lights on the same PCB as the MEMS microphone, the arrangements presented herein run counter to conventional requirements where the indicator lights must be located at the surface of the housing. The arrangements presented herein address this issue by employing optical connectors to optically couple the sub-surface indicator light(s) to the surface of the housing, thereby enabling the indicator light(s) to be visible from outside of the housing and, accordingly, provide their illuminating function.

As noted above, although techniques presented herein are primarily described with reference to MEMS microphones, it is to be appreciated that the techniques presented herein may also be implemented with any other suitable microphone technology now know or later developed that possesses traits similar to those of MEMS microphones. For example, the techniques presented herein may be implemented with other architectures that allow associated PCBs to be located closer to the external surface of the housing, architectures in which the microphones are specifically designed to be rigidly mounted on rigid PCBs, etc.

It is to be appreciated that the embodiments presented herein are not mutually exclusive and that the various embodiments may be combined with another in any of a number of different manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus, comprising:
   a housing including at least one acoustic port;
   a microphone positioned within the housing; and
   at least one light source that is separate from the microphone and positioned within the housing, wherein light emitted from the at least one light source is observable outside of the housing via at least one translucent member located at the at least one acoustic port, and:
   (i) wherein the at least one translucent member is disposed in the at least one acoustic port, and wherein the at least one translucent member is a microphone gasket configured to mount the microphone to the housing and to create an acoustic seal between the microphone and the housing; or
   (ii) wherein the at least one translucent member is disposed in the at least one acoustic port, and wherein the at least one translucent member comprises a microphone membrane configured to be attached to an outer surface of the housing; or
   (iii) wherein the at least one translucent member comprises an optical insert disposed in the at least one acoustic port, wherein the optical housing insert includes a cavity to retain a microphone protector therein; or
   (iv) wherein the microphone is a microelectrical systems (MEMS) microphone electrically mounted on a printed circuit board (PCB) within the housing, and wherein the at least one light source is also electrically mounted on the PCB.

2. The apparatus of claim 1, wherein the microphone gasket is formed from a substantially flexible material and is configured to mechanically isolate the microphone from vibrations delivered to the housing.

3. The apparatus of claim 1, wherein the microphone gasket is formed from a substantially flexible material and includes one or more translucent rigid members extending there through to transport light emitted by the at least one light source to the at least one acoustic port.

4. The apparatus of claim 1, wherein the at least one translucent member comprises the microphone membrane and an optical connector optically coupling the at least one light source to the microphone membrane.

5. The apparatus of claim 1, wherein the MEMS microphone is mounted on a first surface of the PCB and the at least one light source is mounted on a second surface of the PCB, and wherein the first surface of the PCB and the second surface of the PCB are on opposing sides of the PCB.

6. The apparatus of claim 1, wherein the at least one light source comprises one or more light emitting diodes (LEDs).

7. The apparatus of claim 1, the at least one light source comprises an indicator light.

8. The apparatus of claim 1, wherein the at least one translucent member optically couples the at least one light source to an outer surface of the housing via an optical port that is separate from the at least one acoustic port.

9. An apparatus, comprising:
   a housing comprising at least one acoustic port, an outer surface, and an inner surface;
   a printed circuit board (PCB) positioned within the housing adjacent to the at least one acoustic port;
   a microelectromechanical systems (MEMS) microphone disposed in the housing; and
   at least one light source that is separate from the MEMS microphone and mounted on the PCB below the inner surface of the housing, wherein light signals emitted by the at least one light source are observable at the outer surface of the housing via at least one translucent member disposed at the at least one acoustic port, and:
   (i) wherein the at least one translucent member is a microphone gasket configured to mount the MEMS microphone to the housing and to create an acoustic seal between the MEMS microphone and the housing; or
   (ii) wherein the at least one translucent member comprises a microphone membrane configured to be attached to the outer surface of the housing; or
   (iii) wherein the at least one translucent member further comprises an optical housing insert disposed in the at least one acoustic port, wherein the optical housing insert includes a cavity to retain a microphone protector therein.

10. The apparatus of claim 9, wherein the microphone gasket is formed from a substantially flexible material and is configured to mechanically isolate the MEMS microphone from vibrations delivered to the housing.

11. The apparatus of claim 9, wherein the at least one translucent member comprises the microphone membrane and wherein an optical connector optically couples the at least one light source to the microphone membrane.

12. The apparatus of claim 9, wherein the at least one light source comprises an indicator light.

13. The apparatus of claim 9, wherein the at least one light source comprises one or more light emitting diodes (LEDs).

14. An apparatus, comprising:
   a housing including at least one acoustic port;
   a microphone positioned within the housing; and
   at least one light source that is separate from the microphone and positioned within the housing, wherein light emitted from the at least one light source is observable outside of the housing via at least one translucent member located at the at least one acoustic port,
   wherein the microphone is a microelectromechanical systems (MEMS) microphone electrically mounted on a printed circuit board (PCB) within the housing, and wherein the at least one light source is also electrically mounted on the PCB, wherein the MEMS microphone is mounted on a first surface of the PCB and the at least one light source is mounted on a second surface of the PCB, and wherein the first surface of the PCB and the second surface of the PCB are on opposing sides of the PCB.

15. The apparatus of claim 14, wherein the at least one translucent member is disposed in the at least one acoustic port.

16. The apparatus of claim 15, wherein the at least one translucent member is a microphone gasket configured to mount the microphone to the housing and to create an acoustic seal between the microphone and the housing.

17. The apparatus of claim 15, wherein the at least one translucent member comprises a microphone membrane configured to be attached to an outer surface of the housing.

18. The apparatus of claim 14, wherein the at least one translucent member comprises an optical housing insert disposed in the at least one acoustic port, wherein the optical housing insert includes a cavity to retain a microphone protector therein.

19. The apparatus of claim 14, wherein the at least one light source comprises one or more light emitting diodes (LEDs).

20. The apparatus of claim 14, the at least one light source comprises an indicator light.

* * * * *